United States Patent
Wiget et al.

(10) Patent No.: US 11,022,590 B2
(45) Date of Patent: Jun. 1, 2021

(54) ELECTRONIC COMPONENT INCLUDING SENSOR DEVICE AND METHOD OF MANUFACTURING SAME

(71) Applicant: Sensirion Automotive Solutions AG, Stafa (CH)

(72) Inventors: Markus Wiget, Stafa (CH); Stephan Braun, Stafa (CH); Lukas Winkler, Stafa (CH); Markus Graf, Stafa (CH); Lukas Hoppenau, Stafa (CH); Tobias Schmid, Stafa (CH)

(73) Assignee: SENSIRION AG, Stäfa (CH)

( * ) Notice: Subject to any disclaimer, the term of this patent is extended or adjusted under 35 U.S.C. 154(b) by 222 days.

(21) Appl. No.: 16/074,979

(22) PCT Filed: Feb. 3, 2017

(86) PCT No.: PCT/EP2017/052404
§ 371 (c)(1),
(2) Date: Aug. 2, 2018

(87) PCT Pub. No.: WO2017/137325
PCT Pub. Date: Aug. 17, 2017

(65) Prior Publication Data
US 2019/0041372 A1 Feb. 7, 2019

(30) Foreign Application Priority Data

Feb. 11, 2016 (EP) .................................. 16155356
Apr. 1, 2016 (EP) .................................. 16163475

(51) Int. Cl.
*G01N 33/00* (2006.01)
*G01N 27/12* (2006.01)
(Continued)

(52) U.S. Cl.
CPC ....... *G01N 33/0027* (2013.01); *G01N 27/121* (2013.01); *G01N 33/0009* (2013.01); *H01L 23/60* (2013.01); *H01L 27/0248* (2013.01)

(58) Field of Classification Search
None
See application file for complete search history.

(56) References Cited

U.S. PATENT DOCUMENTS

| 5,407,854 A | 4/1995 | Baxter et al. |
| 6,714,392 B2 | 3/2004 | Opolka et al. |

(Continued)

FOREIGN PATENT DOCUMENTS

| CN | 201629903 U | 11/2010 |
| CN | 203387770 U | 1/2014 |

(Continued)

OTHER PUBLICATIONS

European Search Report for application No. EP161553356 dated Aug. 16, 2016, completed on Aug. 4, 2016.

(Continued)

*Primary Examiner* — Jeffrey A Gblende
(74) *Attorney, Agent, or Firm* — Cooper & Dunham LLP

(57) ABSTRACT

An electronic component comprises a carrier (3), a sensor device (2) mounted on the carrier (3), which sensor device (2) comprises a sensor chip (21), and an electrostatic discharge protection element (1) for protecting the sensor chip (21) from an electrostatic discharge, which protection element (1) is mounted on the carrier (3).

22 Claims, 11 Drawing Sheets

(51) Int. Cl.
    *H01L 27/02*    (2006.01)
    *H01L 23/60*    (2006.01)

(56) References Cited

U.S. PATENT DOCUMENTS

| | | | |
|---|---|---|---|
| 9,147,100 B1* | 9/2015 | Lin | G06K 9/00053 |
| 2008/0150050 A1* | 6/2008 | Chou | H01L 23/3185 257/415 |
| 2010/0097205 A1* | 4/2010 | Script | G08B 25/10 340/539.1 |
| 2011/0278703 A1 | 11/2011 | Pagaila et al. | |
| 2013/0305822 A1* | 11/2013 | Graf | G01N 27/048 73/431 |
| 2015/0276472 A1* | 10/2015 | Wang | G06F 3/0317 250/216 |
| 2017/0077696 A1* | 3/2017 | Demenschonok | G06K 9/00053 |

FOREIGN PATENT DOCUMENTS

| | | | |
|---|---|---|---|
| DE | 102007029720 | 6/2007 | |
| FR | 3014094 | 11/2013 | |
| GB | 2484339 | 4/2012 | |
| JP | 2012242253 | 12/2012 | |
| TW | 200939414 A * | 9/2009 | H01L 23/28 |

OTHER PUBLICATIONS

Database WPI Week 201282, Thomson Scientific, London, GBXP-002760519, 2 pages.
Wikipedla entry for Integrated Circuit, 14 pages.
English translation of Chinese official action dated Sep. 1, 2020 in corresponding Chinese Patent Application No. 201780010774.4.

* cited by examiner a)

b)

c)

d)

ELECTRONIC COMPONENT INCLUDING SENSOR DEVICE AND METHOD OF MANUFACTURING SAME

CROSS REFERENCE TO RELATED APPLICATIONS

This application is a § 371 national stage of PCT International Application No. PCT/EP2017/052404, filed Feb. 3, 2017, which is incorporated herein in its entirety by this reference.

TECHNICAL FIELD

The present idea refers to an electronic component and to a method for manufacturing an electronic component.

BACKGROUND ART

Subject to the application, sensors tend to be integrated into sensor chips in today's world of miniaturization. This kind of manufacturing is beneficial in that the size of a sensor device can significantly be reduced compared to a discrete type sensor and a sensing element of such a sensor can be arranged next to electronic circuitry integrated into the very same sensor chip which circuitry may include functions acting on a signal delivered by the sensing element such as amplification, evaluation, etc.

DISCLOSURE OF THE INVENTION

It is a general object of the invention to provide an electronic component including a sensor device with an improved electrostatic discharge protection.

An electronic component according to the features of claim 1 comprises, and a method for manufacturing an electronic component according to claim 28 makes use of a sensor device which sensor device comprises a sensor chip. The sensor chip preferably is a semiconductor chip comprising a semiconductor substrate such as a silicon substrate, and preferably comprising a sensing element, for example sensitive to one or more of a chemical analyte, humidity, a flow of a fluid, a pressure, light or temperature. The sensor chip may, or may not comprise integrated circuitry connected to the sensing element.

The sensor device may in one embodiment consist of the sensor chip, while in a different embodiment, the sensor device may in addition to the sensor chip comprise a package, such that the sensor device is represented by a packaged sensor chip. In a further embodiment the sensor device may comprise the sensor chip and additionally a cap substrate, for example. Preferably, and in particular in case the sensor chip is embodied for sensing an environmental measure such as humidity, a gas or pressure, the electronic component provides an access opening for allowing the medium to be measured to access the sensing element.

The sensor device is arranged on a carrier. The carrier supports the sensor device, and possibly one or more other elements, such as an IC, discrete electrical elements, a plug, etc. The carrier may be one of a printed circuit board, either in a non-flexible or in a flexible form, a ceramic circuit board, or a different kind of a circuit board allowing the elements carried to be electrically interconnected.

The sensor device—and in particular its sensor chip—may be exposed to an electrostatic discharge from the environment which may damage the sensor chip. In order to prevent such damage, an electric discharge protection element—in short: protection element—is arranged on the carrier. This protection element provides for an effective protection of the sensor chip from such electric discharge.

In particular, if the sensor device itself does not include any electric discharge protection, the present approach allows for a still effective protection without the necessity to amend the design of the sensor device, and in particular the sensor chip. Hence, in one embodiment the protection element can be considered as a retrofit solution for protecting a sensor device originally lacking of an electric discharge protection.

In a very preferred embodiment, the protection element is an electrically conductive structure, and in particular is a metallic structure. The protection element may be punched from a sheet of metal, and be folded thereafter to the desired final shape. The material of the protection element in one embodiment is tinned bronze.

The protection element preferably is physically separated from the sensor chip, and preferably is also separated from the sensor device, such that there is no mechanical link there between other than via the carrier, of course, and, if applicable, by a common encapsulation. By this means, an efficient protection is realized by allowing an electric discharge being trapped by the protection element and being electrically isolated from the sensor chip. Preferably, a minimum distance between the protection element and the sensor device is 0.1 mm. This is beneficial in preventing flash-arcs.

In case of the carrier being a circuit board comprising circuit paths, it is preferred that the circuit board also comprises a contact, and preferably a contact pad for a ground connection, and preferably for ground connecting the electronic component. The protection element preferably is electrically connected to this contact for draining any electric discharge trapped to ground. The circuit board may include an electrically conducting path between the ground contact and the protection element.

In a preferred embodiment, the protection element exceeds the sensor device in height. Hence, the protection element is more attractive to trap an electric discharge than the sensor chip and/or the sensor device, respectively.

In one embodiment, the protection element comprises, and preferably consists of a rod including a single terminal mounted on the carrier. In a very preferred embodiment, such protection element includes a portion extending into a space above the sensor device.

In a different embodiment, the protection element comprises a bridging structure including at least two, and preferably one of exactly two, three or four terminals resting on the carrier. Such protection element spans the sensor device at a distance. Such arrangement favors the trapping of electrical discharges. In addition, such protection element offers an enhanced mechanical stability given that the at least two of its terminals rest on the carrier. In a different embodiment, the bridging structure not only spans the sensor device but also one or more other chips in case such chips being present on the carrier.

In a preferred embodiment, the sensor device is configured to sense a parameter of the environment, such as a flow of a fluid, light, temperature, gas, humidity, or pressure. In such example, a sensing element may be arranged on or integrated at a front side of the sensor chip which front side faces away from the carrier when the sensor chip is mounted onto the carrier.

In many of the above applications, the sensing element requires an access to the environment for performing a sensing of the desired environmental variable. If in such case the sensor device comprises a package in addition to the sensor chip, the package preferably includes an access opening for allowing access to the sensing element. Preferably, the package of the sensor device protects the sensor chip from mechanical impact and/or light, and may seal the chip against an undesired impact of liquids or gases. In a preferred embodiment, the package may cover at least parts of the sensor chip in form of an encapsulation, e.g. in form of a mold compound. The material used may preferably be a resist, in particular a dry resist, for example SU-8. Or, the package may be an element formed separate from the chip and may be attached to the chip later on, for example, by gluing, bonding, etc. Here, the package may be a silicon-on-insulator, or other semiconducting layer arrangement. The package may be made from one of a semiconductor, silicon, silicon and a silicon-oxide coating, silicon and a solderable coating, ceramic, ceramic and a silicon-oxide coating, ceramic and a solderable coating, glass, glass and a silicon-oxide coating, glass and a solderable coating, metal, metal and a solderable coating, dielectric material and a polymer.

In such sensor device, the sensor chip typically is arranged on a support such as a leadframe, which leadframe includes a die pad for arranging the sensor chip on, and contact pads electrically connected to the sensor chip, e.g. by means of bond wires. The encapsulation partly encapsulates the chip except for the access opening, and partly encapsulates the leadframe, e.g. except for the contact pads and/or the die pads. The access opening may take the form of a recess in the package thereby exposing the sensitive element to the outside world. If in such case the protection element has the shape of a bridging structure and at least partly bridges the sensor device, it is desired that the bridging structure is designed in geometry and arranged relative to the sensor device such that on the one hand an effective electric discharge protection is realized, and that on the other hand a sensing function of the sensor chip is not impaired by the protection element. In a preferred embodiment, the bridging structure spans an area of a top surface of the sensor device that is between a third and half of the entire top surface of the sensor device.

Preferably, the sensor device has a rectangular footprint owed to a typical rectangular footprint of the sensor chip diced out of a wafer. The sensor device preferably has contact pads exposed at least at a bottom surface of the sensor device, and preferably at edges of the sensor device. In case the sensor device only provides contact pads along two opposing edges of its footprint—also referred to as first pair of edges—such sensor device may also be referred to as DFN (Dual-Flat No-Leads). In case the sensor device provides contact pads along all edges of its footprint such sensor device may also be referred to as QFN (Quad-Flat No-Leads).

It is preferred, that such sensor device is SMD-mounted (Surface Mounted Device) to the carrier. The carrier shows contact pads being prepared with a contact material such as a solder paste prior to the sensor device being placed onto the carrier. After having placed the sensor device onto the carrier with its contact pads being aligned with the contact pads of the carrier and hence being deposited onto the solder paste, the electrical connections are established by heating the solder paste. In such scenario, it is preferred that solder joints remain optically inspectable, and preferably automatically optically inspectable, for verifying the electrical connection between the sensor device and the carrier.

Taking the desire for an automated optical inspection of the electrical connections into account, it is preferred that the bridging structure is arranged on the carrier such that it does not affect the automated optical inspection of the electrical connections. Hence, in case of a DFN package with contact pads arranged along the first pair of edges, it is preferred that the terminals of the bridging structure are arranged facing the sensor device at a second pair of opposed edges of its rectangular footprint. However, in a different embodiment, the sensor device may be represented by a QFN package even if optical inspection accessibility to two edges of the sensor device is limited owed to the arrangement of the bridging structure protection element.

While in one embodiment of the present invention—and provided the sensor chip has a rectangular footprint—the bridging structure is arranged to bridge the sensor device in parallel to one of a longitudinal or lateral extension of the sensor chip, in a different embodiment, the bridging structure is arranged to bridge the sensor device diagonally.

In a different embodiment of the present invention, however, still including the bridging structure as protection element, such bridging structure is arranged not to bridge the sensor device. Instead, the bridging structure is arranged next to the sensor device and/or the sensor chip respectively. In order to provide an effective electric discharge protection, it is preferred that a maximum distance between the bridging structure and the sensor device is 5 mm.

In a preferred embodiment, the protection element is a multi-use element. The protection element not only serves as an electric discharge protection element, but can also be used for mounting a housing to the carrier. In particular when the protection element is embodied as a bridging structure, the protection element in combination with a mounting element of the housing provides for a fixture for the housing. The mounting element on the housing side may include one or more clamps which are clamped to the protection element thereby securing the housing to the carrier. The housing may protect the sensor device and/or any further electronics from mechanical and/or fluid impact. The housing preferably is made from plastics and in a mounted state is clamped to the bridging structure.

In a different class of embodiments, the sensor device and the protection element each are partly encapsulated by the same encapsulation. This embodiment preferably refers to the sensor device including a packaged sensor chip including the package and an access opening in the package. Preferably, this class of embodiments does not apply to a sensor device consisting of a bare semiconductor chip. However, it could apply to a capped semiconductor chip, e.g. capped by a silicon or other type cap.

Accordingly, in case of a sensor device including a packaged sensor chip, it is preferred that the encapsulation is applied after the sensor device and the protection element are arranged on the carrier such that the encapsulation at least partly encapsulates the sensor device and the protection element each, in view of the sensor device comprising the access opening in its package which preferably is not encapsulated by the encapsulation. On the other hand, at least a portion of the protection element remains uncovered from the encapsulation, and hence exposed in order to trap electrical charges. With respect to the sensor device, the encapsulation hence may encapsulate the package, however, e.g. leaving the access opening in the package uncovered. Hence, the encapsulation preferably also comprises an ingress via which ingress access to the sensor chip is granted. Accordingly, a medium to be measured may reach a sensing element of the sensor chip through the ingress of the encapsulation and through the access opening of the package. Accordingly, it is preferred that the access opening in the package and the ingress in the encapsulation are aligned, or at least are connected in order to allow the supply of the medium towards the sensing element. Given that the encapsulation is applied to the arrangement containing the sensor device and the protection element both attached to the carrier, it is preferred that the encapsulation also partly encapsulates the carrier.

The encapsulation may protect the sensor device, and also the protection element.

Preferably, the encapsulation is created by a molding process, and specifically by one of
injection molding;
low pressure injection molding;
transfer molding; in all of which processes a molding compound is inserted into a mold, preferably in a liquid or a low viscosity state, and solidifies thereafter as encapsulation.

Most preferably, the encapsulation is created by a hotmelt molding or potting process representing a low pressure injection molding process. The hotmelt, which preferably is a thermoplastic adhesive, preferably is injected into the mold in a molten state and solidifies thereafter. The hotmelt may be one of Polyurethane, Polyamide, Polyolefine, Ethylen-Copolymere, Blockcopolymere or Polyester. This processing is preferred in that the sensor device is exposed to less heat and to less pressure than in injection molding. Preferably, in hotmelt molding the mold remains at room temperature while the molten hotmelt preferably is injected into the mold at a temperature in a temperature range between 130° C. and 180° C. for a Polyurethane based hotmelt, and at a temperature in a temperature range between 180° C. and 240° C. for a Polyamide based hotmelt. A temperature at the devices to be molded remain significantly below these temperatures in view of the hotmelt cooling down immediately when meeting the device and acting as a thermal insulator while at the same time the mold acts as a heat sink. However, this molding process still offers a desired low viscosity of the hotmelt at reasonable temperatures. One of the advantages is that owed to the lower pressure the hotmelt is injected into the mold—i.e. at pressures between 5 bar and 40 bar, compared to pressures of 100 bar to 1000 bar in injection molding—usage of an elastic film protecting structures during molding can be avoided. In case a cable e.g. is mounted or connected to the carrier, the hotmelt preferably partly encapsulates the cable and/or preferably the electrical connection between the cable and the carrier, too. Hence, the hotmelt can act as a protection element for the cable as well as any electrical or mechanical connection between the cable and the carrier. Since the solidified hotmelt still is a rather soft, it can react flexible on movement of the cable. In case the hotmelt adheres to the cable, it can absorb any tension or torsion stress acting on the cable.

It is explicitly noted in this context that encapsulating the arrangement by a hotmelt is considered as a variant of molding given that for the subject purpose a mold is provided into which the material to be molded is injected/filled into.

In contrast, it is preferred that the package of the sensor device is manufactured by injection or transfer molding. Accordingly, it is preferred that different molding processes are applied sequentially for building the package first and the encapsulation thereafter. Transfer molding preferably makes use of a duroplast (Epoxide) as mold compound, which may be injected into the mold by a pressure up to a maximum of 100 bar. Injection molding is widely known and makes use of pressures up to 400 bar.

In case the protection element shows a bridge structure and rests on the carrier with at least two terminals while a horizontal portion of the protection element bridges the access opening of the sensor device, it is preferred that such protection element also bridges the ingress. Accordingly, the horizontal portion of the bridges structure preferably extends above the access opening of the sensor device while it spans the ingress thereby, e.g. emerging from side walls of the encapsulation defining the ingress. In a different embodiment, the protection element may protrude from a top surface of the encapsulation and extends above the ingress.

The same holds in case the protection element is represented by single terminal element such as a rod. Such protection element may either emerge from a side wall of the encapsulation defining the ingress and reach into the ingress, or may emerge from a top surface of the encapsulation and be formed so as to reach into the space above the ingress. This may be achieved either by a prebent protection element, or by bending the protection element after having applied the encapsulation. In a third alternative, the protection element may be bent by the mold used for encapsulating the sensor device, e.g. in response to closing the mold.

In case the protection element is of a bridge structure, a horizontal portion of the bridge spanning the ingress and the access opening may also be attributed n a function during manufacturing the encapsulation: A part of the mold, and specifically a plunger used for forming the ingress, preferably needs to cover the access opening of the sensor device to prevent molding compound or other contamination to access the sensor chip. However, the horizontal portion of the bridge structure may be arranged distant from the top surface of the sensor device and hence, distant from the access opening. Accordingly, it is preferred that the plunger not only rests on the horizontal portion of the protection element during molding but pushes the horizontal portion towards the top surface of the sensor device, and specifically towards the package including its access opening, in response to closing the mold. Accordingly, during molding, the horizontal portion of the protection element may at least partially rest or be in contact with the package of the sensor device such that it seals the access opening, or, in case the horizontal portion comprises an opening, that the plunger covers the opening while the horizontal portion seals the access opening. In this state mold compound preferably is filled into the mold.

In one embodiment, the protection element is designed such its deformation evoked by the mold is not reversible and the protection element remains deformed after molding. In such state, the protection element preferably does not exert mechanical stress on the encapsulation. In a different embodiment, the protection element may be designed as elastic element such that its deformation evoked by the mold as such would be reversible. However, after the mold compound is solidified, the encapsulation urges the protection element to remain in its deformed state. In such state, the protection element may exert mechanical stress on the encapsulation. In both scenarios, however, it is preferred that the elastic modulus of the protection element in combination with the dimensioning of the mold is selected such, that the mold is prevented from exerting exceeding pressure onto the sensor device when being closed. In this regard, the protection element not only serves as an element for protecting the sensor chip from electric discharge, but at the same time protects the sensor chip and the entire sensor device during encapsulating the sensor device, and hence acts as a spacer during the encapsulation process.

When the horizontal portion of the protection element is meant to rest on the sensor device after encapsulation, it is preferred that it has an opening that preferably is aligned with the access opening of the sensor device after encapsulating. This allows the medium to be measured to reach the access opening in the package and finally the sensing element.

In case the protection element is not bridge structured but rather an element containing a single terminal, the same concept may apply as indicated above: The plunger of the mold may—in the process of being moved towards the sensor device when closing the mold—capture a free end of the protection element on purpose, and thereby deform the protection element. In particular, the free end may be bent by the mold from its previous vertical position orthogonal to the plane of the carrier into a horizontal position in parallel to the plane of the carrier. A predetermined bending point in the protection element and/or a guide in the mold may support the desired deformation.

However, in a different approach, the rod shaped protection element is not deformed on purpose during closing the mold but remains un-deformed. In this example, the plunger of the mold directly sits on the sensor device when the mold is closed, in order to cover the access opening.

A mechanical impact of the mold may be alleviated by applying an elastic film either to the plunger, or to the sensor device, in any case spanning the access opening. Additionally, surface irregularities are balanced. Such elastic film may also be applied during molding in connection with the bridge structured protection element. The first variant where the film is attached to the mold is also known as film assisted molding. In the latter variant, the film may be permanently attached to the sensor device and not be removed after molding. Accordingly, such elastic film later on acts as a membrane for further protecting the sensor chip and shielding the access opening from contamination etc. In such case, it is desired to select a material of the film that not only is elastic but also is permeable to the medium to be measured, such as a gas or a liquid. Such material may be a perforated PTFE, for example.

In case of the protection element having a single terminal and a free end which is not deformed on purpose when applying the mold, it is preferred that after molding the encapsulation the free end emerging from the encapsulation is bent in order to bring it closer to the sensor chip. Preferably, the free end reaches into the ingress after bending. A middle portion of the protection element between the terminal and the free end remains encapsulated.

In a different approach, a component is prefabricated which component contains a partly encapsulated protection element, the encapsulation of which is referred to as encapsulation member. At a bottom surface of this encapsulation member, the one or more terminals of the protection element is exposed. This component may then be mounted onto the carrier with its bottom surface facing a top surface of the carrier. In one embodiment, it is only the one or more terminals of the protection element that provides for the mechanical mounting of the component to the carrier, which at the same time serves for an electrical connection to the carrier. In this approach, it is preferred that the sensor device remains uncovered by the encapsulation member. Preferably, the encapsulation member encircles the sensor device.

In a different embodiment, a housing is provided for at least a part of the carrier. In this embodiment, the sensor device preferably is premounted to the carrier. The housing, e.g. in form of a plastic housing may have an opening in order to grant access to the sensor device. In this embodiment, the protection element again is preferred to have a bridge structure, and to actually bridge the sensor device after being mounted to the carrier. Again, at least two terminals of the protection element rest on the carrier and preferably are electrically connected thereto. However, each terminal may comprise an extension that preferably is arranged on a common level together with a horizontal portion of the protection element bridging the sensor. In a first variant, the protection element is attached to the carrier prior to the housing being attached to the carrier. Accordingly, the housing may finally be attached to the carrier by e.g. elements of the housing being clamped between the carrier and the extensions of the protection element. Or, the housing may be brought into its desired position with respect to the carrier, and the extensions of the protection element may be bent into a form fit with the elements of the housing in order to fix the housing in this position.

Preferably, the electronic component is used in an automotive application.

According to another aspect of the present invention, a method is provided for manufacturing an electronic component. A sensor device is provided including contact pads as well as an electrostatic discharge protection element including at least one terminal. This order in providing the sensor device and the protection element is arbitrary and may be reversed.

The sensor device is arranged on a carrier with the contact pads facing the carrier, and the protection element is arranged on the carrier with its one or more terminals facing the carrier. Again, this order is arbitrary and may be reversed.

Preferably, once both the sensor device and the protection element are arranged on the carrier, a common reflow soldering step is applied to both the sensor device and the protection element. The common reflow soldering step in particular may comprise a heating of a solder paste arranged between the contact pads/terminals of the sensor device and the protection element on the one hand and contact pads of the carrier on the other hand, thereby electrically and/or mechanically connecting the sensor device and the protection element to the carrier.

This present idea results in an effective protection of the sensor chip including any circuitry from an electric discharge. Accordingly, an electronic component is provided including a protection element for protecting from electrical discharge which protection element comprises at least one terminal mounted on and/or resting on the carrier. The protection element can be reflow soldered on the carrier together with the sensor device to protect from electrical discharge, or it can be pressed or snapped or clipped in or to the carrier by way of its one or more terminals.

Preferably, the protection element is shaped not to encase the sensor device. Hence, it is preferred that the protection element is not a closed structure in form of a cap capping the sensor device. Instead, the protection element preferably is shaped according to one or more of: not to fully encircle the sensor device; not comprising a wall in complete form fully encircling the sensor device; not of rectangular footprint.

Embodiments disclosed in connection with the component shall also be considered disclosed in connection with the method and vice versa.

Other advantageous embodiments are listed in the dependent claims as well as in the description below.

BRIEF DESCRIPTION OF THE DRAWINGS

The embodiments defined above and further embodiments, features and advantages of the present invention can also be derived from the examples of embodiments to be described hereinafter in connection with the drawings in which the figures illustrate.

MODES FOR CARRYING OUT THE INVENTION

Figure 1:
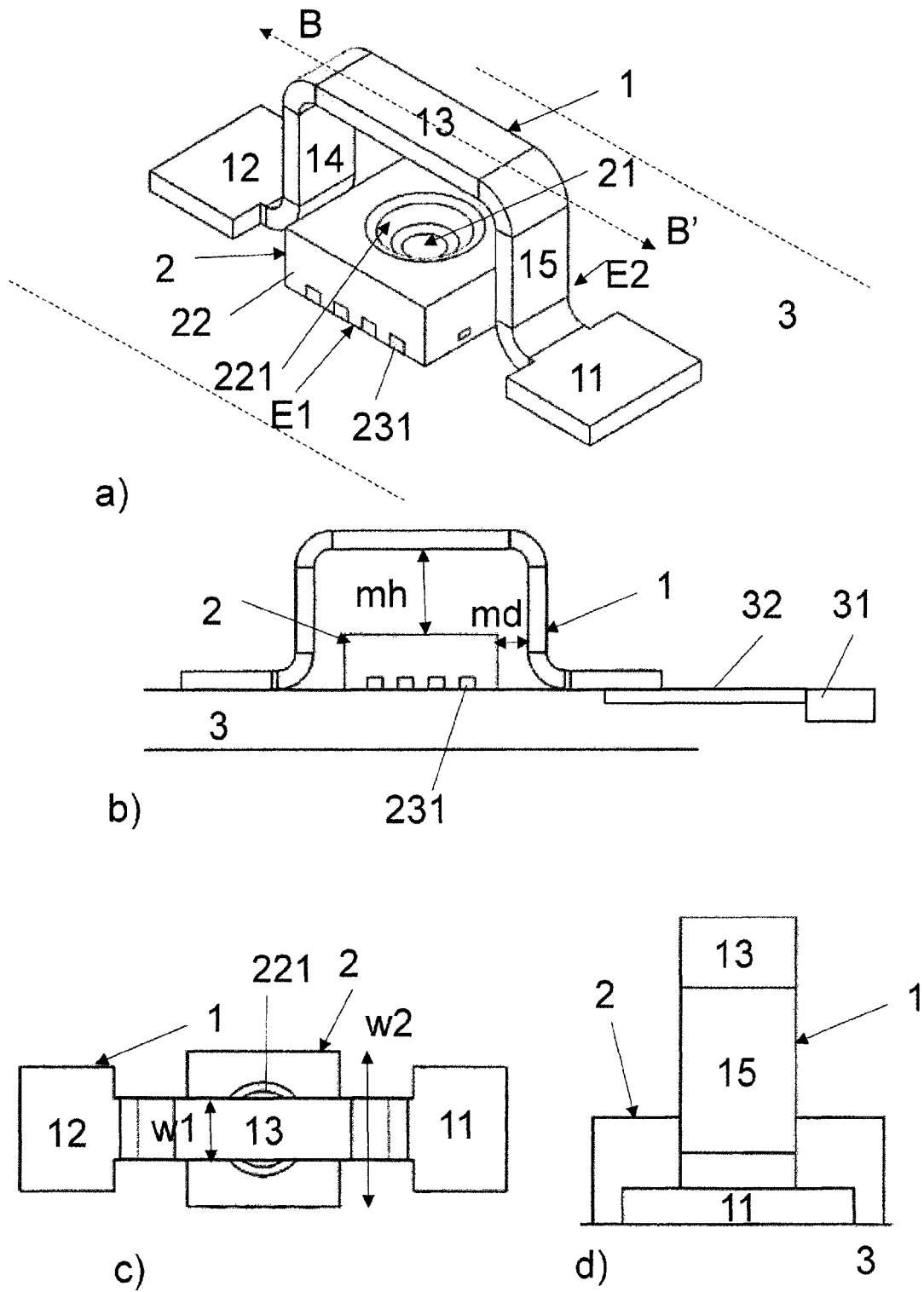
FIG. 1 an electrical component according to an embodiment of the present invention, in diagram a) in a perspective view, in diagram b) in a side cut, in diagram c) in a top view, and in diagram d) in a side view.

FIG. 1 illustrates an electronic component according to an embodiment of the present invention. The electronic component includes at least an electric discharge protection element 1, a sensor device 2, and a carrier 3, but may contain additional elements not shown. The electronic component is shown in a perspective view in diagram a), in a side cut along line B-B' in diagram b), in a top view in diagram c), and in a side view in diagram d).

The carrier 3, for example, is a printed circuit board. The protection element 1 and the sensor device 2 are arranged on a front side of the carrier 3. In the present embodiment, the protection element 1 has the shape of a bridging structure that is arranged to bridge the sensor device 2. The protection element 1 contains two terminals 11 and 12 resting on the carrier 3. The bridging structure further includes two vertical portions 14 and 15, and a horizontal portion 13. The protection element 1 is a single piece made from a metal or any other electrically conducting material, and preferably is punched and bent into its present shape.

The sensor device 2 is a packaged sensor chip 21 containing the sensor chip 21 and a package 22 in form of an encapsulation. The sensor chip 2 is arranged on a leadframe. Portions of the leadframe build contact pads 231 that are exposed at a bottom face of the sensor device 2 and as such face the carrier 3. In addition, portions of these contact pads 231 are exposed from side walls of the package 22 as can be seen in diagrams 1a) and 1b). The package 22 comprises an access opening 221 in form of a recess in a top surface of the package 22 for granting access to the sensor chip 2, and in particular for granting access to a sensitive element that is exposed from the package 22 by means of the access opening 221.

As can be derived from diagram 1b), the protection element 1 is electrically connected to a ground contact 31 of the carrier 3, via a conductor 32. Hence, any electrical discharge trapped by the protection element 1 is drained to the ground contact 31.

A horizontal portion 13 of the protection element 1 spans the sensor device 2, and in particular spans a part of the access opening 221, since the exposed sensor chip 21 including the sensing element is most endangered by an electrical discharge. As can be seen from diagram 1c) it is not the entire surface of the sensor device 2 that is covered by the horizontal portion 13 of the protection element 1. Instead, a width w1 of the horizontal portion 13 is less than a width w2 of the sensor device 2 which ensures that the exposed portion of the sensor chip 2 receives a sufficient amount of the medium to be measured. Preferably, between a third and half of the top surface/footprint of the sensor device 2 is spanned by the protection element 1.

As can be seen from diagrams 1a) and 1b), the protection element 1 is arranged distant from the sensor device 2. Preferably, a distance md, which reflects a distance between a side wall of the sensor device 2 and the portion of the protection element 1 facing this side wall is equal to or less than 10 mm to prevent a direct discharge into the sensor device 2 on the one hand, and preferably is equal to or more than 0.05 mm, in order to prevent an arc-over on the one hand.

When it comes to a height relation between the sensor device 2 and the protection element 1, it is preferred that the protection element 1 exceeds the sensor device 2 in height as can be derived from diagrams 1a) and 1b). In particular, a minimum height distance mh between the protection element 1 and the sensor device 2 is 1 mm.

As can be derived from diagram 1a), the contact pads 231 are arranged at an edge E1 of the sensor device 2 that does not face a terminal 11, 12 of the protection element 1. Hence, electrical connections—also referred to as solder joints in this context—between the carrier 3 and the contact pads 231 remain inspectable, and in particular optically inspectable. The sensor device 2 may comprise further contact pads 231 and solder joints at the opposed edge E2 which are optically inspectable in the same manner.

Figure 2:
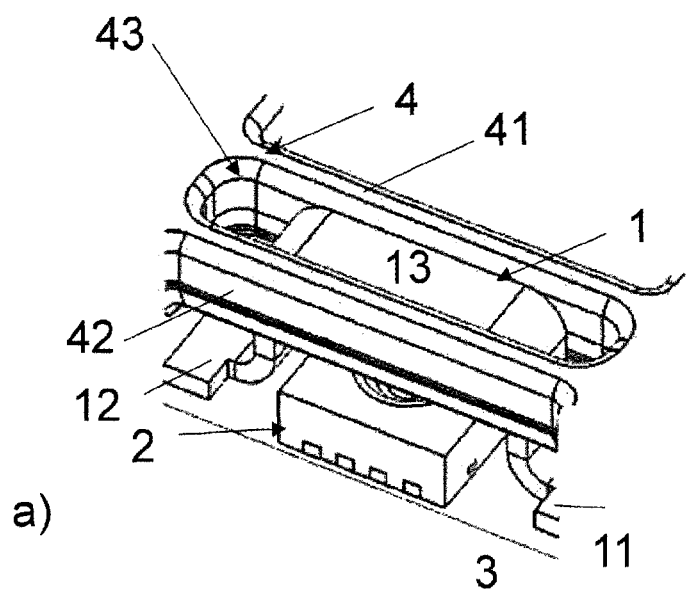
FIG. 2 an electrical component according to an embodiment of the present invention, in diagram a) in a perspective view, and in diagram b) in a lateral cut.
Figure 2:
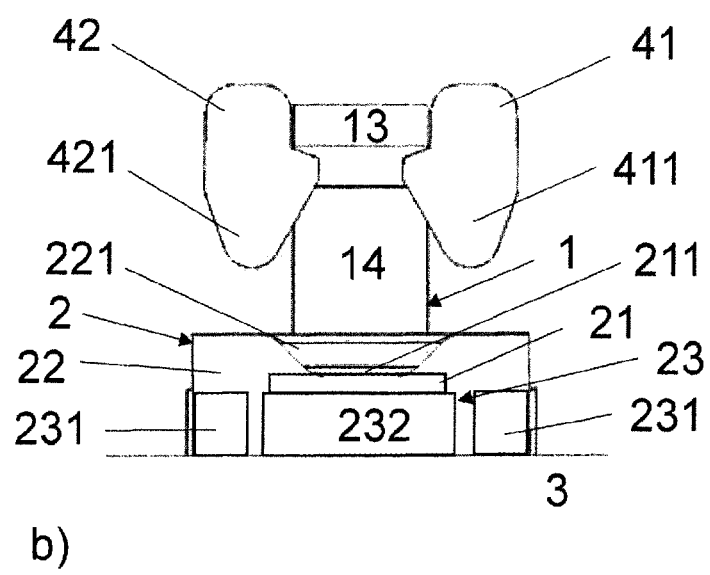

FIG. 2 illustrates an electrical component according to an embodiment of the present invention. Diagram 2a) illustrates its perspective view, while diagram 2b) shows the electronic component in a lateral cut. The basic elements such as the protection element 1, the sensor device 2 and the carrier 3 may be identical to the ones shown in FIG. 1, or may be of different shape and/or arrangement. In addition, the present electronic component includes a housing 4, e.g. made from plastics, only a portion of which housing 4 is shown, and which housing 4 shall protect the sensor device 2 and possibly any other elements arranged on the carrier 3.

The housing 4 has two bars 41 and 42 forming an opening 43 there between. The bridge structured protection element 1 reaches into the opening 43, in particular with its horizontal portion 13, a top surface of which remains exposed to the outside world for trapping electrical discharges. Remainders of the opening not n filled of the protection element 1 are dimensioned such that a sufficient amount of the medium reaches the sensor chip underneath.

The two bars 41 and 42 each comprise an integrated clamp 411, 421, which clamp into the horizontal portion 13 of the protection element 1. Hence, the housing 4 and the carrier 3 are attached, such that the protection element 1 not only serves for draining an electric discharge but also serves for mounting the housing 4 to the carrier 3.

According to the cut view shown in diagram 2b), the sensor device 2 comprises the sensor chip 21 arranged on a die pad 232 of a leadframe 32. In addition, contact portions 231 are made from the leadframe 23 and are connected to the sensor chip 2, e.g. by bond wires not shown. An encapsulation in form of a package 22 encloses portions of the sensor chip 21 and the leadframe 23. An access opening 221 in the package 22 provides access to a top surface of the sensor chip 21 including a sensitive element 211 being exposed through the access opening 221.

The sensor chip 21 preferably is a semiconductor chip with a substrate, such as a silicon substrate, and a stack of material layers such as a CMOS layer stack on top of the substrate. The sensing element 211 is integrated into the sensor chip 21, e.g. is arranged in the stack of material layers in the present example. The sensing element 211 may be connected by means of at least two electrodes, such as interdigitated electrodes. The sensing element 211 may cover the electrodes.

Figure 3:
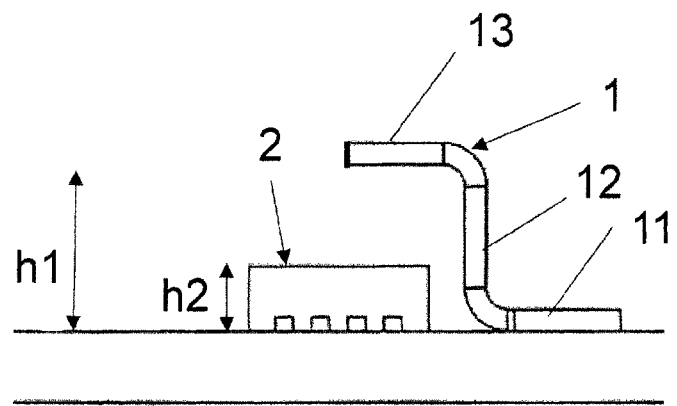
FIG. 3 an electrical component in a side cut, according to an embodiment of the present invention.

FIG. 3 illustrates an electrical component in a side cut according to an embodiment of the present invention. In contrast to the protection element 1 introduced in FIG. 1, the present protection element 1 is not of a bridge shape but rather of a rod shape including a single terminal 11 only. In addition, a vertical portion 12 holds a horizontal portion 13 reaching into a space above the sensor device 2 for providing an effective discharge protection. Notably, a height h1 of the protection element 1 exceeds a height h2 of the sensor device 2. The protection element 1 is arranged separate from the sensor device 2. It is preferred, that the single terminal 11 in combination with the rest of the protection element 1 is configured in its dimension and/or weight such that a center of gravity of the protection element is configured to make the protection element 1 remain in an upright position after being placed on the carrier 3 for surface mounting. The overall shape of the protection element in this embodiment may be considered as a step.

Figure 4:
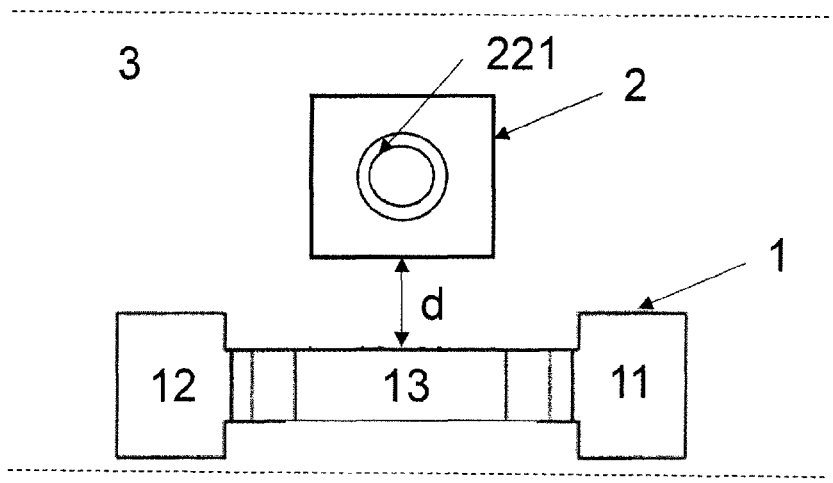
FIG. 4 an electrical component in a top view, according to an embodiment of the present invention.

FIG. 4 illustrates an electrical component according to another embodiment of the present invention, in a top view. Although the protection element 1 again is bridge shaped such as in FIG. 1, the protection element 1 now is arranged next to the sensor device 2, in particular at a distance d from the sensor device 2. This arrangement also provides an effective protection from an electric discharge. A housing (not shown) may be attached to the protection element 1 in the same manner as introduced with respect to FIG. 2.

Figure 5:
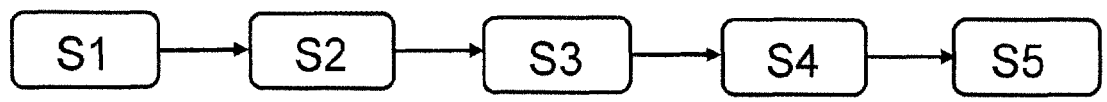
FIG. 5 a method for manufacturing an electronic component according to an embodiment of the present invention.

FIG. 5 illustrates a method for manufacturing an electronic component according to an embodiment of the present invention. In step S1, a sensor device is provided, the sensor device including contact pads. In step S2, an electrostatic discharge protection element is provided, the protection element including at least one terminal. In step S3, the sensor device is arranged on a carrier with the contact pads facing the carrier. In step S4, the protection element is arranged on the carrier with the terminal facing the carrier. In step S5, the contact pads and the at least one terminal are reflow soldered in a common reflow soldering step.

Steps S1 and S2 can be interchanged in order. Steps S3 and S4 can be interchanged in order. Steps S1 and S3 can be performed in sequence, followed by steps S2 and S4. Steps S2 and S4 can be performed in sequence, followed by steps S1 and S3.

In a preferred embodiment, the carrier is provided prepared, by having attached solder paste to the contact pads of the carrier the protection element and the sensor device are to be deposited on with their corresponding contact pads and terminals. Hence, a placement of the sensor device and the protection element onto the carrier includes a placement onto the solder paste. The common reflow soldering step may then include a heating of the solder paste for generating a sound electrical connection between the carrier and the sensor device and between the carrier and the protection element.

FIGS. 6 to 10 each shows an electrical component in a top view, according to embodiments of the present invention. In each of these embodiments, the protection element 1 is shaped as a bridging structure bridging a sensor device 2. The sensor device 2 preferably is a packaged sensor chip 21, but could take any other form of sensor device 2, too.

Figure 6:
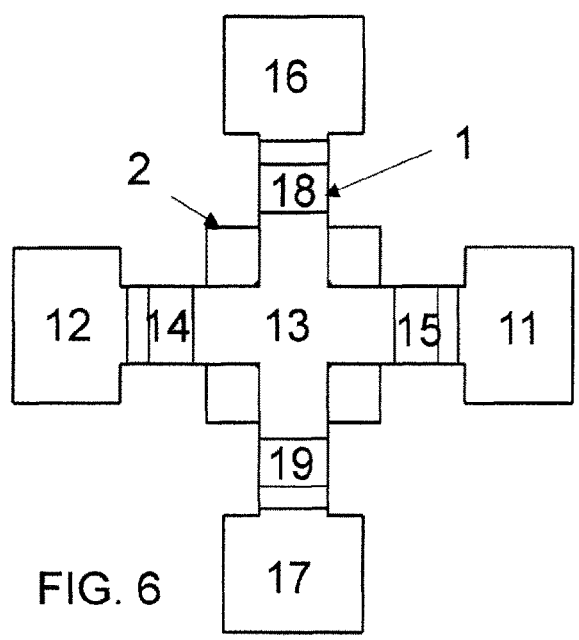
FIGS. 6 to 10 each an electrical component in a top view, according to embodiments of the present invention.

Instead of two terminals 11 and 12, the protection element 1 of FIG. 6 has four terminals 11, 12, 16 and 17 resting on the carrier. Accordingly, four vertical portions 14, 15, 18 and 19 are provided in the bridging structure, as well as a cross-shaped horizontal portion 13. This embodiment provides for an excellent mechanical stability.

Figure 7:
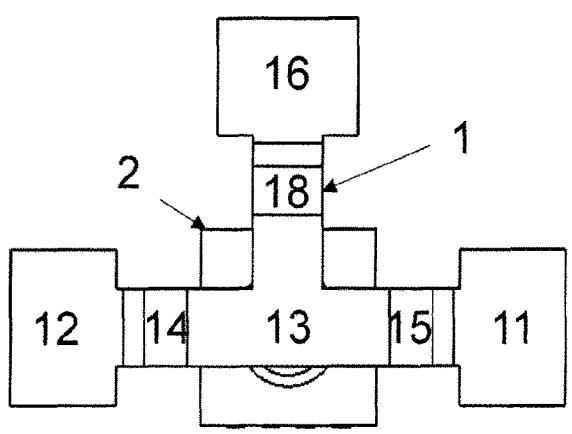

The protection element 1 of FIG. 7 has three terminals 11, 12 and 16 resting on the carrier. Accordingly, three vertical portions 14, 15, and 18 are provided in the bridging structure, as well as a T-shaped horizontal portion 13. This embodiment also provides for an excellent mechanical stability.

Figure 8:
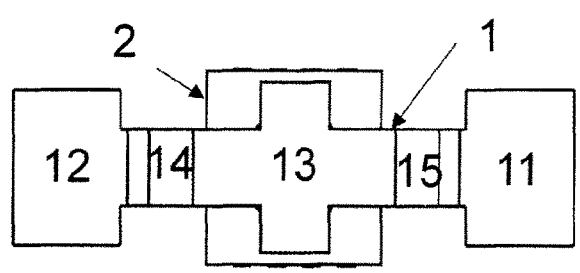

The protection element 1 of FIG. 8 has two terminals 11, 12. In comparison with the embodiment shown in diagram 1c), the present horizontal portion 13 has cross-like extensions as such providing a bigger coverage of the sensor device 2 and as such providing an even better electric discharge protection.

Figure 9:
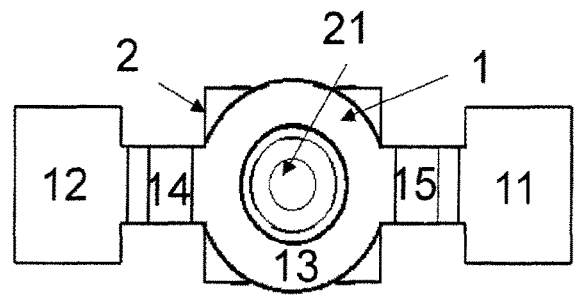

The protection element 1 of FIG. 9 has two terminals 11, 12, and a ring-shaped horizontal portion 13. Through the ring-shaped horizontal portion 13 an excellent access is provided to the sensor chip 21 for the medium to be measured, while at the same time the increased area of the ring-shaped horizontal portion 13 provides an excellent coverage of the sensor device 2 and as such provides an excellent electric discharge protection.

Figure 10:
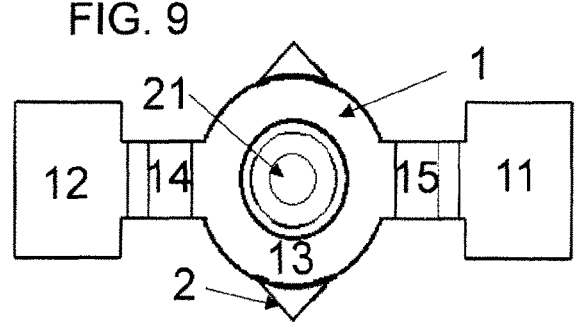

In the embodiment of FIG. 10, the protection element 1 is identical to the protection element 1 of FIG. 9. However, its orientation is different with respect to the sensor device 2. While in the embodiment of FIG. 9, the basic orientation of the protection element 1 is in parallel to the edges of the sensor device 2 with its rectangular footprint, the protection element 1 of FIG. 10 is aligned diagonally across the sensor device 1. This orientation may also be implemented for any other shape of protection element 1.

Again, it is preferred that for any of the previous embodiments the protection element 1 is a single piece made from a metal or any other electrically conducting material, and preferably is punched and bent into its present shape.

Figure 11:
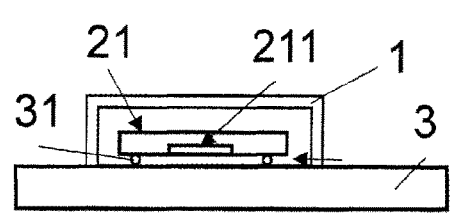
FIGS. 11 to 14 each an electrical component in a side cut, according to an embodiment of the present invention, FIG. 15 an electrical component, in a side cut in diagram a) and in a perspective view in diagram b), according to an embodiment of the present invention.

FIG. 11 illustrates an electrical component in a side cut, according to an embodiment of the present invention. In this embodiment, the sensor device is represented by a sensor chip 21 with a sensing element 211 of the sensor chip 21 facing the carrier 3. Hence, the sensor chip 21 is flip-chip mounted onto the carrier 3 by means of e.g. solder balls 31. Access is granted to the sensing element 211 from sideways—as indicated by the arrow—through a gap between the sensor chip 21 and the carrier 3. The protection element 1 bridges the sensor chip 2.

Figure 12:
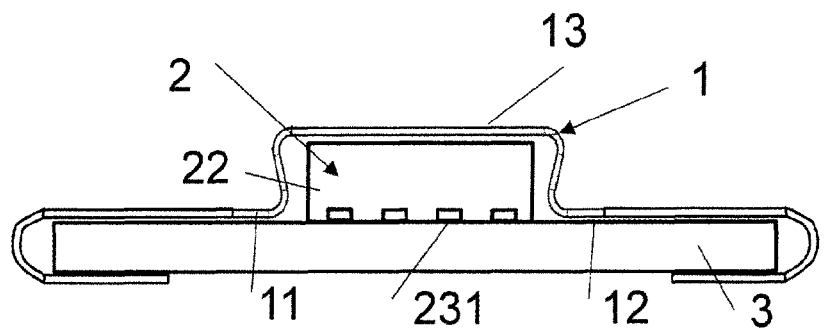

FIG. 12 illustrates an electronic component in a cut view according to an embodiment of the present invention. The sensor device 1 is a packaged sensor chip comprising a package 22, contact pads 231 exposed from the package 22 and a sensor chip inside the package 22 (not visible). It is assumed that an access opening (not visible) is comprised in the package 22 in its top surface for granting access to a sensing element of the sensor chip. Similar to the embodiment of FIG. 1, the protection element 1 is a bridge structure including a horizontal portion 13 extending in parallel to the plane of the carrier 3, which horizontal portion 13 spans the sensor device 2, and in particular spans the access opening. However, in this embodiment the protection element 1 extends beyond the terminals 11 and 12 and wraps around the carrier 3, thus, giving the protection element 1 the shape and function of a bracket. Hence, in such embodiment, the protection element 1 may simply be clipped to the carrier 3. While in one embodiment, the terminals 11 and 12 may still be soldered to the carrier 3, in a different embodiment no such soldering is applied, and a sufficient electrical connection and mechanical support may be achieved just by the bracket shaped protection element 1 sitting tight on the carrier 3. In an embodiment, the protection element 1 may be electrically connected to metallizations arranged on a backside/bottom surface of the carrier 3, i.e. opposite its front side/top surface to which the sensor device 2 is attached. In this embodiment, the extensions wrapping around the carrier 3 can rather be considered as terminals 11 and 12.

Figure 13:
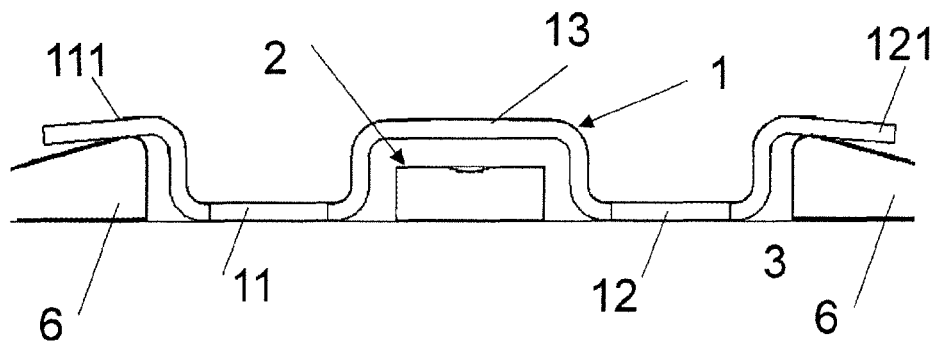

FIG. 13 illustrates another embodiment of an electronic component according to an embodiment of the present invention. Again, the sensor device 2 preferably is a packaged sensor chip including an access opening (not visible). In this embodiment, a housing 6, e.g. premanufactured, shall be attached to the carrier 3 thereby preferably being in contact with the carrier 3. Preferably, the housing 6 does not cover the sensor device 2. Instead a gap is provided between the housing 6 and the sensor device 2. In one embodiment, the protection element 1 is mounted to the carrier 3 carrying the sensor device 2 first. The protection element 1 preferably is a bridge structure so as to bridge the sensor device 2. However, the protection element 1 preferably shows extensions 111 and 121 at each of its terminals 11 and 12. These extensions 111 preferably extend to a level elevated with respect to the level of the terminals 11 and 12. In a second step, the housing 6 may be clipped or snapped under or otherwise attached to the extensions 111, 121 of the protection element 1. In a possible final step, the extensions 111, 121 may be deformed in order to provide for a long lasting form-fit with the housing 6 thereby attaching the housing 6 to the carrier 3. Hence, the protection element 1 has two-fold functionality, i.e. ESD protection, and mechanical fixation at the same time. In an assembled state, these extensions 111, 121 contribute to a form fit with the housing 6. The present protection element 1 may be prefabricated, e.g. by bending into the shape as shown. Preferably, the level the extensions 111, 121 reach to the same level of the horizontal portion 13. The protection element 1 may comprise more than two terminals 11,12 and preferably is soldered by its two or more terminals 11,12 to corresponding metallizations of the carrier 3. However, the protection element 1 may instead by otherwise attached and electrically connected to the carrier 3. In one embodiment, the housing 6 may provide means such as guides, snap fits, etc., to facilitate the orientation of the protection element on the carrier 3, and/or to support the attachment between the housing 6 and the protection element 1.

Figure 14:
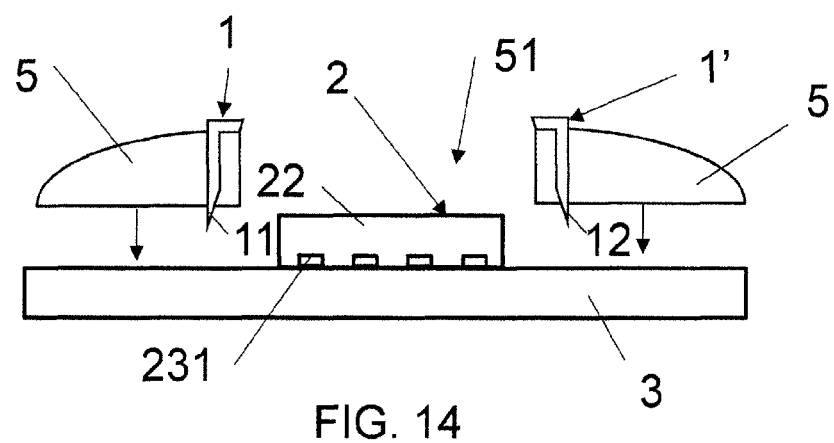

FIG. 14 illustrates another embodiment of an electronic component according to an embodiment of the present invention. Again, the sensor device 1 preferably is a packaged sensor device 2 including contact pads 231 and a package 22 partly covering a sensor chip, and an access opening (not visible) in the package 22 to allow a medium to be sensed to reach the sensor chip. In the state shown in FIG. 14, the sensor device 2 is mounted to a carrier 3. A component comprising an encapsulation member 5 and a protection element 1 is not finally mounted to the carrier 3 yet. The component preferably is prefabricated, by partly encapsulating the protection element 1, preferably in a molding process. The encapsulation member 5 comprises a bottom surface presently facing a top surface of the carrier 3 the sensor device 2 is arranged on. The at least one terminal 11 of a first protection element 1 is exposed from the bottom surface of the encapsulation member 5 and the at least one terminal 12 of another first protection element 1' is exposed from the bottom surface of the encapsulation member 5 to enable mounting of the component to the top surface of the carrier 3 as is indicated by the arrows. The component preferably is prefabricated and mounted to the carrier 3 as a whole. In one embodiment, the component may be mounted to the carrier 3 solely by means of the one or more terminals 11 of the protection element 1, e.g. by soldering or pressing into or snapping into the carrier 3. The protection element 1 may, as presently shown, include two individual elements in form of rods, or a single protection element 1 including two or more terminals. In case of one or more single terminal protection elements 1, a free end of each protection element 1 may be bent after being encapsulated as is shown in FIG. 14. In a different embodiment, the protection element 1 as shown in FIG. 14 may be a single protection element 1 including a single terminal 11 encircling the sensor device 2 but not bridging it. Preferably, after mounting the component to the carrier 3, the sensor device 2 is not in contact with the encapsulation member 5. The encapsulation member 5 can be considered to comprise an ingress 51 in form of an opening that allows medium to pass to the sensor device 2. Preferably, the encapsulation member 5 includes additional mounting means such as snap fits to mount the component to the carrier 3.

Figure 15:
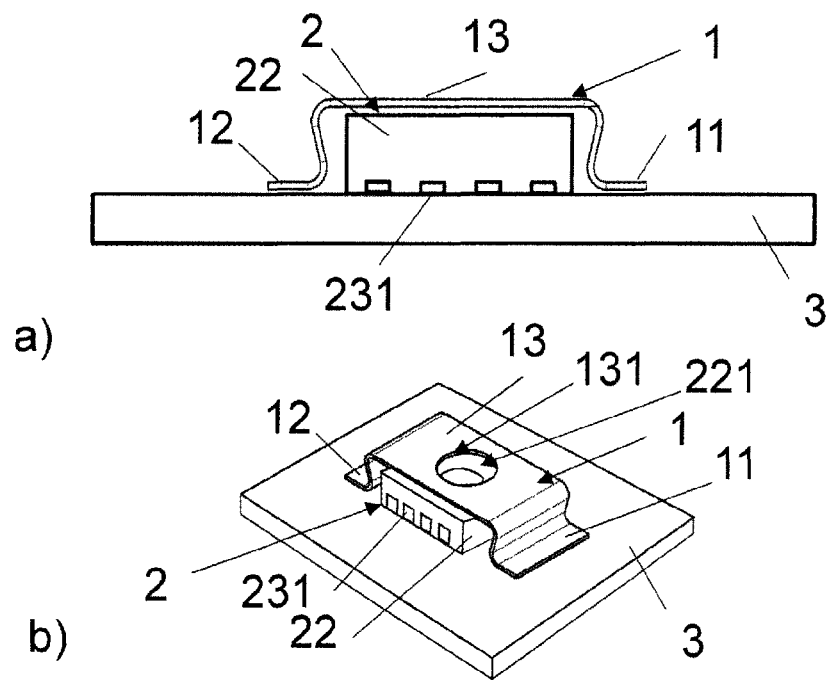

FIG. 15 illustrates another embodiment of an electronic component according to an embodiment of the present invention. The cut view in diagram 15b) resembles the electrical component of FIG. 1b). A bridge structured protection element 1 bridges a packaged sensor device 2, the package 22 and contact pads 231 of which are shown. The protection element 1 includes a horizontal portion 13 spanning the sensor device 2, while terminals 11 and 12 rest on the carrier 3 and are electrically connected thereto. From the perspective view of diagram 15b) it can be derived that the present protection element 1 has an opening 131 in its horizontal portion 13 that allows access to the underlying access opening 221 of the sensor device 2. The electronic component of FIG. 15 may represent a complete electrical component, or may represent an intermediary product.

Figure 16:
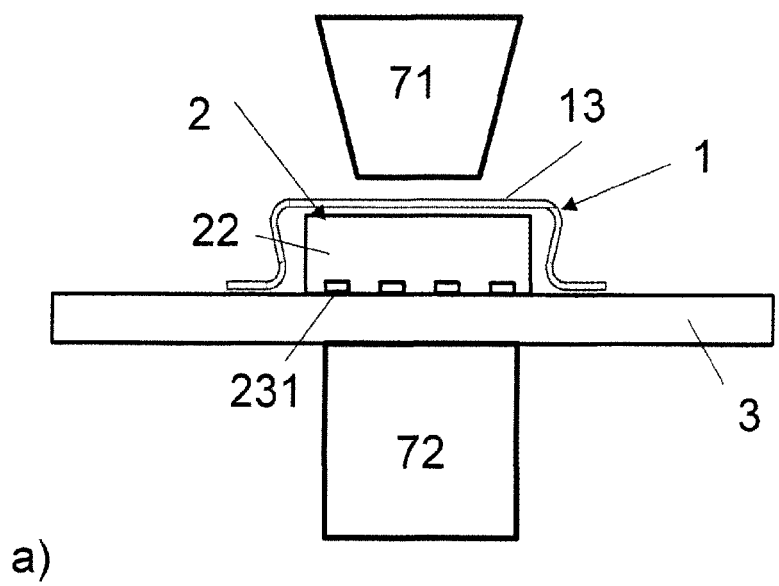
FIG. 16 a method for manufacturing an electrical component, according to an embodiment of the present invention.
Figure 16:
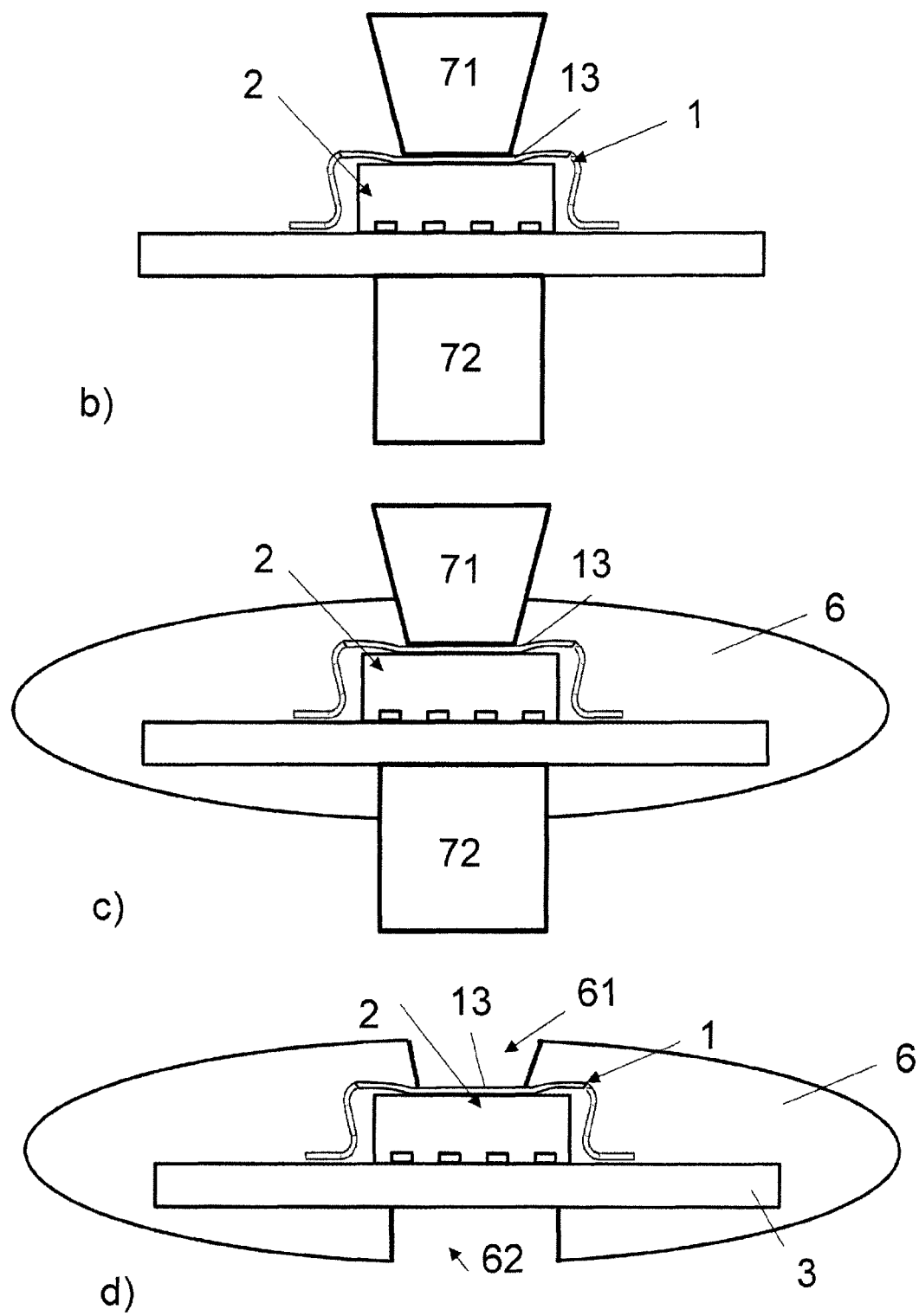

In the latter case, FIG. 16 illustrates a method for manufacturing an electrical component according to an embodiment of the present invention, starting from the intermediary product of FIG. 15: According to the diagram 16a), an arrangement including the sensor device 2 and the protection element 1 both mounted onto the carrier 3 is inserted in an (open state) of a mold 71,72 presently represented by a plunger 71 acting from the top and a support 72 acting from the bottom. Presently, the support 28 evokes an access to the backside of the carrier 3 in the future encapsulation. Of course, the support 72 of the mold may take different shapes subject to the needs. For example, the support 72 may be supporting the entire backside of the carrier 3, such that the backside of the carrier 3 remains totally exposed from the future encapsulation. In a different embodiment, the support 72 may e.g. only engage with the sides of the carrier 3 such the backside of the carrier 3 becomes completely encapsulated by the future encapsulation.

When closing the mold 71,72 i.e. moving the plunger 71 and the support 72 towards each other, e.g. by clamping, the plunger 71 sits on the horizontal portion 13 of the protection element 1, and in the following deforms the protection element 1. This deformed state of the protection element 1 is shown in diagram 16b). It is assumed that closing the mold 71, 72 is controlled not to exert too much pressure on the sensor device 2 resulting in a damage. However, as can be derived from diagram 16b), the closing of the mold 71,72 may result in the horizontal portion 13 of the protection element 1 at least partly resting on the sensor device 2, in particular on its package 22.

In the step shown in diagram 16c), a mold compound is applied into/to the mold 71,72, preferably in form of a hotmelt, thereby generating an encapsulation 6. Of course, in this case the mold not only consists of plunger 71 and support 72 but contains more elements (not shown) responsible for forming the outer shape of the encapsulation 6. The final product is illustrated in diagram 16d): The plunger 71 has caused an ingress 61 in the encapsulation 6 for the medium to be sensed to reach the sensor device 2, and in particular the sensor chip embedded in the sensor device 2. The access opening in the package 22 of the sensor device 2 opens to the top and leads into the ingress 61. Another recess 62 is built in the encapsulation 6 resulting from the support 72 of the mold 71,72, which in different embodiments may not be needed.

As can be derived from diagram 16d), the protection element 1 preferably is permanently deformed, in order to reduce mechanical stress in the encapsulation 6.

Figure 17:
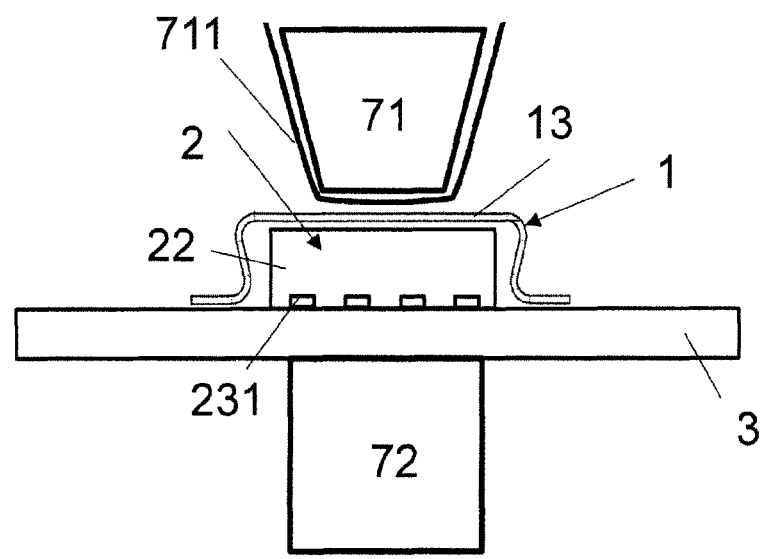
FIGS. 17 and 18 modifications in the method according to FIG. 16, according to embodiments of the present invention.
Figure 18:
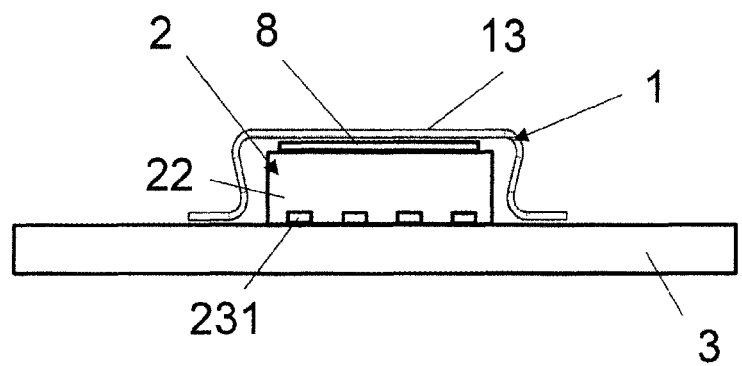

FIGS. 17 and 18 illustrate modifications in the method for manufacturing the electronic component according to FIG. 16 according to embodiments of the present invention. According to FIG. 17, the plunger 71 may be covered by an elastic film 711 that reduces mechanical stress on the protection element 1 during molding, and hence, protects the protection element 1. The elastic film 711 preferably is attached to the plunger 71 or is applied between the protection element 1 and the plunger 71, and will be removed after molding.

According to FIG. 18, an elastic film 8 is preferably placed on a top surface of the sensor device 2, i.e. between the sensor device 2 and the protection element 1. When the plunger 71 exerts pressure on the horizontal portion 13 of the protection element 1 and pushes it towards the sensor device 2, the film 8 protects the sensor device 2, and in particular its package 22. Since the film 8 is assumed to span the access opening in the package 22, it is preferred that the film 8 not only is elastic but also is permeable to the medium to be sensed given that it is not envisaged to remove the film 8 after molding. In addition, the elastic film can enhance a sealing of the access opening in the sensor device (not visible) in order to prevent hotmelt residuals to enter the access opening from the side while the plunger 71 is applied. In a different embodiment, the film 8 is removed after molding. In addition, the elastic film 8 as well as the elastic film 711 of FIG. 17 support the generation of smooth surfaces of the encapsulation.

Figure 19:
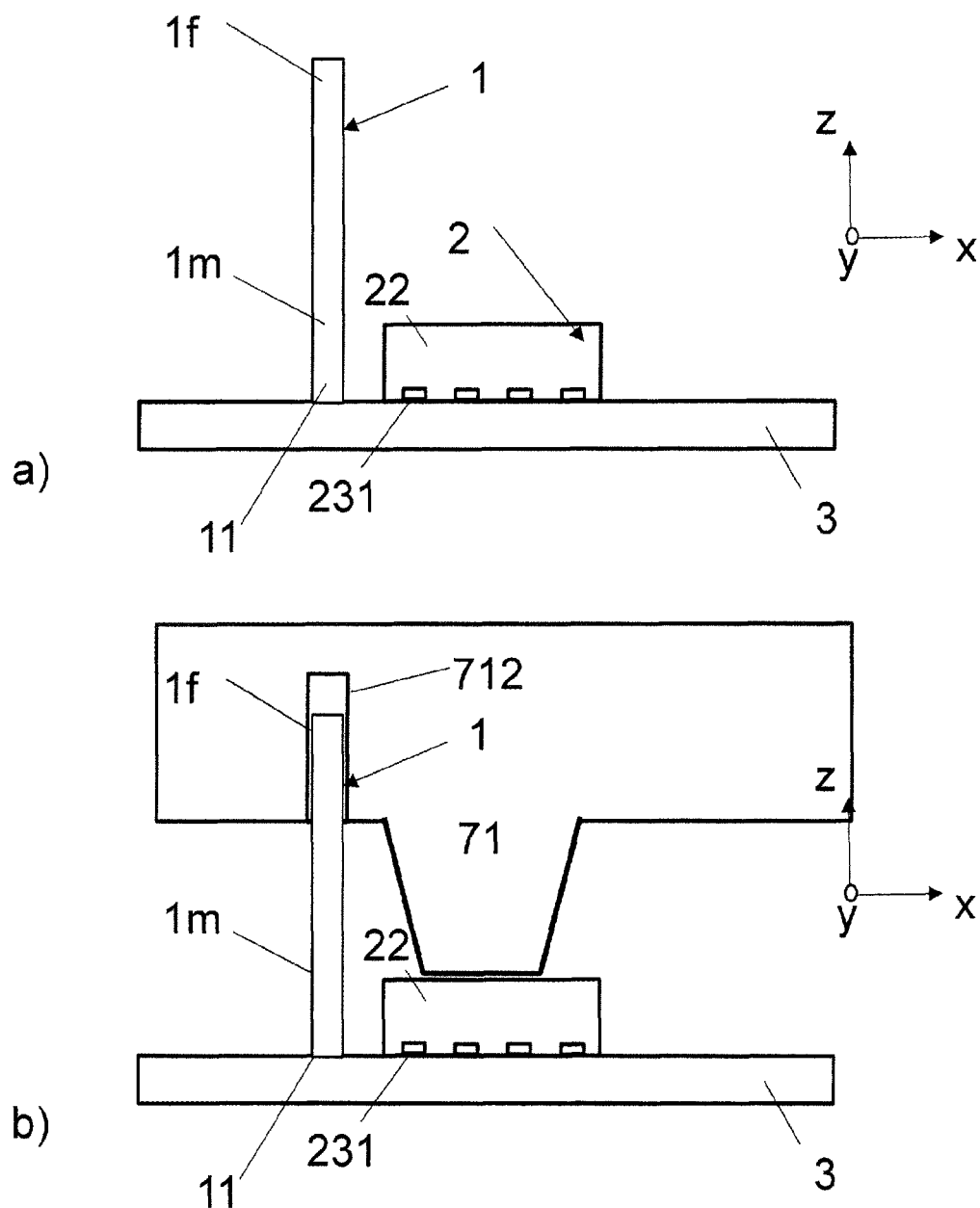
FIG. 19 another method for manufacturing an electrical component, according to an embodiment of the present invention.
Figure 19:
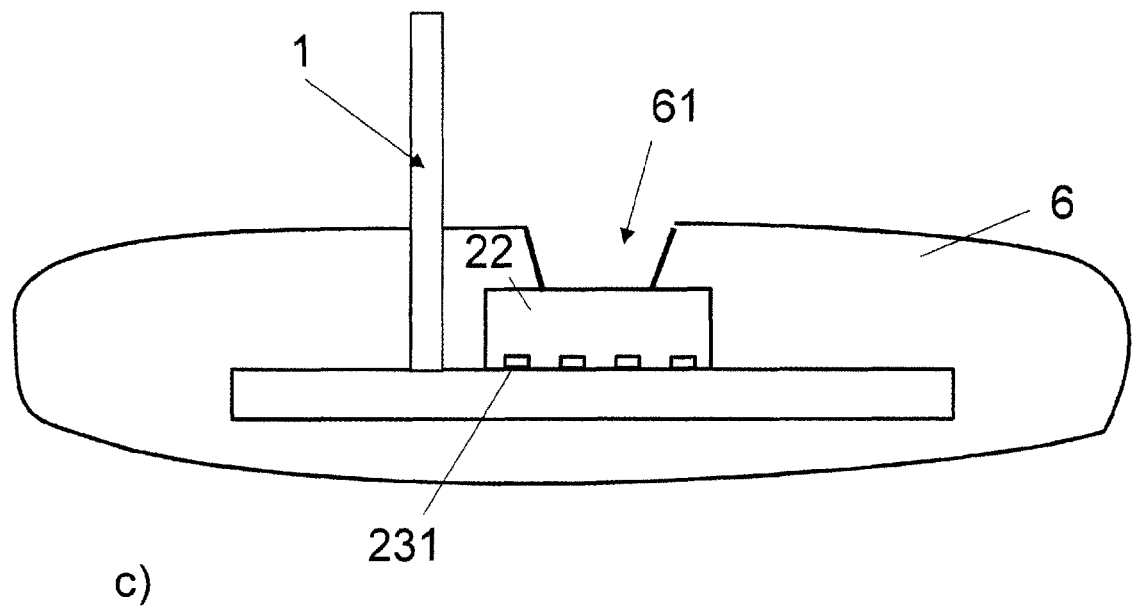
Figure 19:
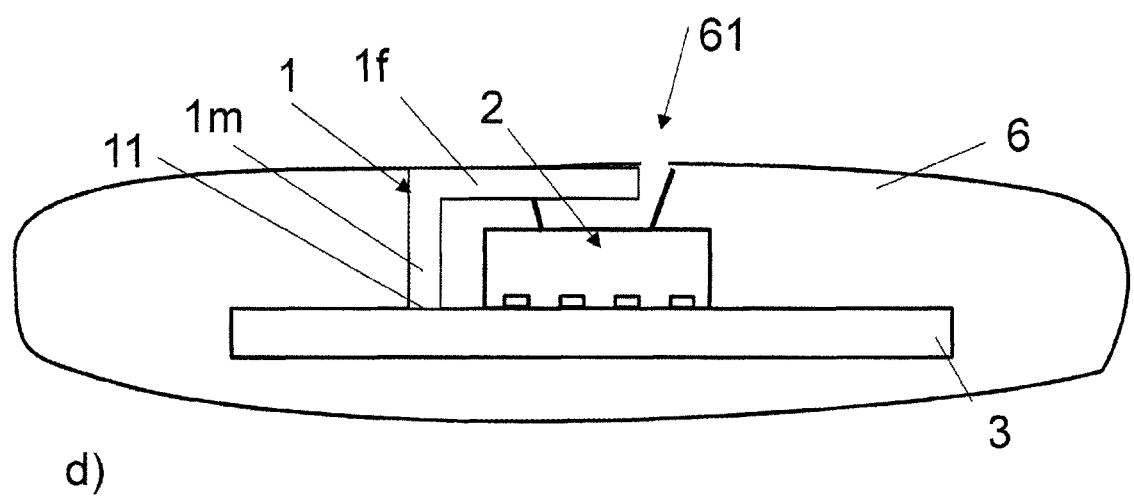

FIG. 19 illustrates another method for manufacturing an electronic component according to an embodiment of the present invention. Again it is started from an electrical component that in one embodiment is a final product, but in another embodiment represents an intermediary product that is similar to the intermediary product shown in FIG. 15. Instead of the bridge structured protection element 1 of FIG. 15, a single terminal 11 protection element 1 in form of a rod is used and presently extends in z-direction orthogonal to the plane x/y defined by the carrier 3, see diagram 19a). The protection element 1 has the single terminal 11 by which it is mounted to the carrier 3, a free end 1f, and a middle portion 1m between the terminal 11 and the free end 1f.

In a next step the arrangement of diagram 19a) is inserted into a mold containing a plunger 71, see diagram 19b). The mold may additionally contain a receptacle 712 for the rod shaped protection element 1, in particular its free end 1f. However, the mold may include multiple more shapes/elements. The plunger 71 does not directly act on the protection element 1 but sits on the sensor device 2 when being closed, optionally protected by an elastic film such as shown in FIG. 17 or in FIG. 18. After having applied a mold compound, an encapsulation 6 is formed, see diagram 19c). The encapsulation 6 encloses the carrier 3, portions of the sensor device 2, but leaves an ingress 61 towards the sensor device 2. The protection element 1 protrudes from the encapsulation 6 by its free end 1f while the middle portion 1m thereof is covered and enclosed by the encapsulation 6.

In a next step shown in diagram 19d), the free end 1f of the protection element 1 is bent into a horizontal position extending into the ingress 61 and hence improving its function as electrical discharge protection. It can be derived from diagram 19c), that the free end 1f terminates at the same level as the encapsulation 6: Hence, the free end 1f may be bent while the mold compound of the encapsulation 6 still is in a deformable state so as to press the free end 1f of the protection element 1 into the encapsulation 6. In a different embodiment, the plunger 71 includes a lateral protrusion to build a channel in the upper surface of the encapsulation 6 extending from the rim of the ingress 61 into which channel the free end 1f of the protection element 1 is bent, preferably after the mold compound is hardened.

Figure 20:
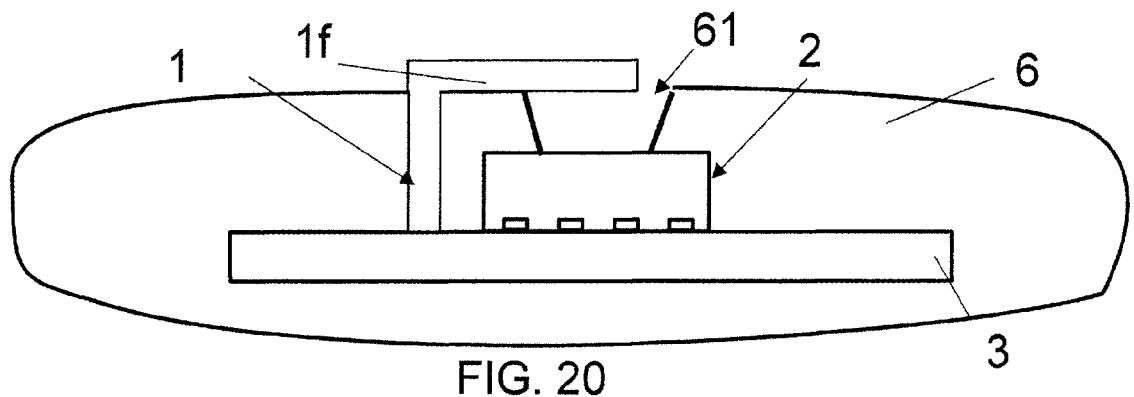
FIGS. 20, 21 and 22 modifications in the method and the resulting electronic component of FIG. 19, according to embodiments of the present invention.
Figure 21:
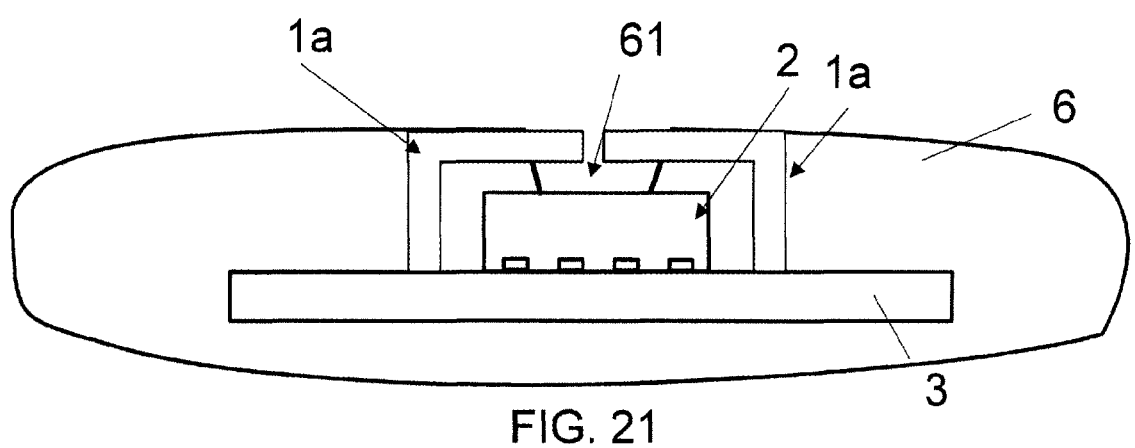

FIGS. 20 and 21 show modifications in the method of FIG. 19 and in the resulting electronic component, according to embodiments of the present invention. In each of the embodiments, the final bending step is concerned. In the embodiment of FIG. 20, the free end 1f of the protection element 1 protrudes from the encapsulation 6 even after bending. Accordingly, it is assumed that the free end 1f is bent after the mold compound forming the encapsulation 6 is hardened. In the embodiment of FIG. 21, the bending is performed in the same manner as in the example of diagram 19c). However, two rod shaped protection elements 1 are provided instead of a single one. The free end 1f of each protection element 1 is bent towards the ingress 61 and reaches into the ingress 61.

Figure 22:
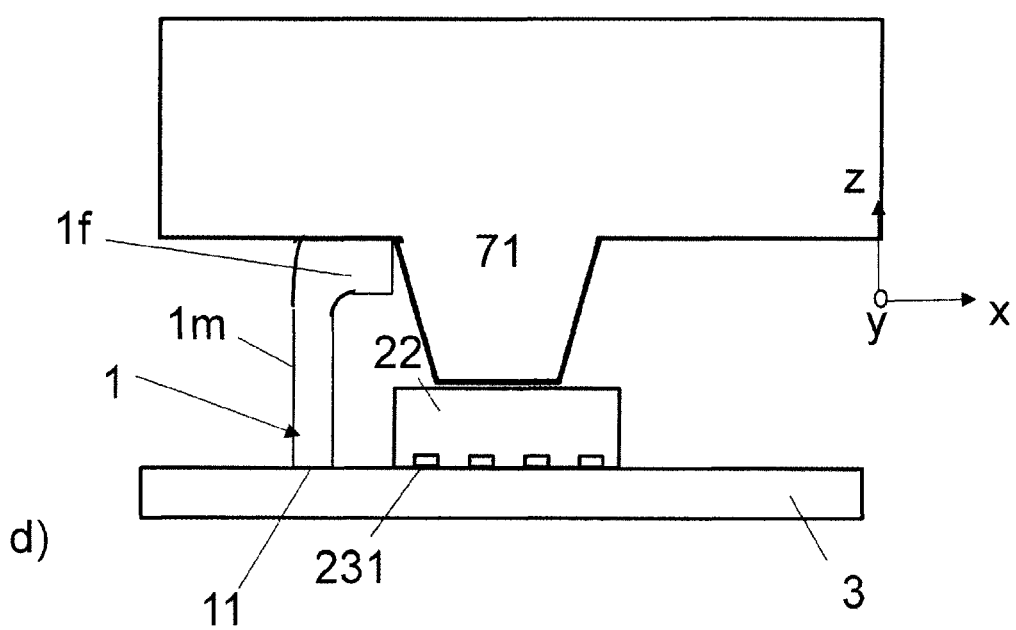

FIG. 22 shows a variant of FIG. 19b): While there, a receptacle is provided in the mold for the rod shaped protection element that remains in its vertical position after molding, the receptacle 712 of FIG. 19b) is not provided in the example of FIG. 22. Instead, the free end 1f of the protection element 1 is pre-bent such that its free end is inclined towards the carrier 3 and will be bent when closing the mold halves, and preferably is bent towards the ingress in the encapsulation that will be produced by the plunger 71. Accordingly, in this embodiment, closing the mold and bending the protection element 1 is achieved in a single step.

While there are shown and described presently preferred embodiments of the invention, it is to be distinctly understood that the invention is not limited thereto but may be otherwise variously embodied and practiced within the scope of the following claims.

The invention claimed is:

1. An electronic component, comprising:
a carrier;
a sensor device mounted on the carrier, said sensor device comprising a sensor chip;
an electrostatic discharge protection element mounted on the carrier, for protecting the sensor chip from an electrostatic discharge, the protection element comprising
a bridging structure including at least two terminals resting on the carrier, wherein the protection element is arranged to bridge the sensor device, or
a rod including a single terminal mounted on the carrier, wherein the rod includes a portion extending into a space above the sensor device,
wherein the protection element has two terminals,
wherein the sensor device has a rectangular footprint with a first and a second pair of opposed edges, and the sensor device comprises contact pads arranged along the first pair of opposed edges of the rectangular footprint, and
wherein the terminals of the protection element are arranged facing the sensor device at the second pair of opposed edges of the rectangular footprint.

2. The electronic component according to claim 1,
wherein the sensor device comprises a package in addition to the sensor chip,
wherein the sensor chip comprises a sensing element arranged on or integrated at a specific side of the sensor chip,
wherein the package comprises an access opening for providing access to the sensing element, and
wherein the protection element is physically separated from the sensor device.

3. The electronic component according to claim 1,
wherein the sensor device consists of the sensor chip or comprises a cap substrate in addition to the sensor chip,
wherein the sensor chip comprises a sensing element arranged on or integrated at a specific side of the sensor chip, and
wherein the protection element is physically separated from the sensor device.

4. An electronic component:
a carrier;
a sensor device mounted on the carrier, said sensor device comprising a sensor chip; and
an electrostatic discharge protection element mounted on the carrier, for protecting the sensor chip from an electrostatic discharge, the protection element comprising
a bridging structure including at least two terminals resting on the carrier, wherein the protection element is arranged to bridge the sensor device, or
a rod including a single terminal mounted on the carrier, wherein the rod includes a portion extending into a space above the sensor device,
wherein the sensor device comprises a package in addition to the sensor chip,
wherein the sensor chip comprises a sensing element arranged on or integrated at a specific side of the sensor chip,
wherein the package comprises an access opening for providing access to the sensing element,
wherein the specific side of the sensor chip faces in a direction away from the carrier, and
wherein the protection element is arranged to bridge at least a part of the access opening.

5. An electronic component, comprising:
a carrier;
a sensor device mounted on the carrier, said sensor device comprising a sensor chip; and
an electrostatic discharge protection element mounted on the carrier, for protecting the sensor chip from an electrostatic discharge, the protection element comprising
a bridging structure including at least two terminals resting on the carrier, wherein the protection element is arranged to bridge the sensor device, or
a rod including a single terminal mounted on the carrier, wherein the rod includes a portion extending into a space above the sensor device,
wherein the sensor device consists of the sensor chip or comprises a cap substrate in addition to the sensor chip,
wherein the sensor chip comprises a sensing element arranged on or integrated at a specific side of the sensor chip, facing the carrier,
wherein an access opening is provided between the sensor chip and the carrier for granting access to the sensing element, and
wherein the protection element is arranged to bridge the sensor chip.

6. The electronic component according to claim 1,
wherein the carrier is a circuit board,
wherein the carrier comprises a contact for a ground connection, and
wherein the protection element is electrically connected to the contact for ground connection.

7. The electronic component according to claim 1, further comprising an encapsulation disposed on the carrier to partly encapsulate the sensor device and partly encapsulate the protection element, wherein the encapsulation partly covers the carrier.

8. An electronic component, comprising:
a carrier;
a sensor device mounted on the carrier, said sensor device comprising a sensor chip;
an electrostatic discharge protection element mounted on the carrier, for protecting the sensor chip from an electrostatic discharge, the protection element comprising
a bridging structure including at least two terminals resting on the carrier, wherein the protection element is arranged to bridge the sensor device, or
a rod including a single terminal mounted on the carrier, wherein the rod includes a portion extending into a space above the sensor device; and
an encapsulation disposed on the carrier to partly encapsulate the sensor device and partly encapsulate the protection element,
wherein the encapsulation comprises an ingress for providing access to the sensing element, and
wherein a non-encapsulated portion of the protection element is disposed to emerge from the encapsulation and to at least partly bridge the ingress.

9. The electronic component according to claim 8, wherein a portion of the protection element rests on the sensor device.

10. An electronic component, comprising:
a carrier;
a sensor device mounted on the carrier, said sensor device comprising a sensor chip;

an electrostatic discharge protection element mounted on the carrier, for protecting the sensor chip from an electrostatic discharge, the protection element comprising
  a bridging structure including at least two terminals resting on the carrier, wherein the protection element is arranged to bridge the sensor device, or
  a rod including a free end and additionally including a terminal end forming a single terminal mounted on the carrier, wherein the rod includes a portion extending into a space above the sensor device; and
an encapsulation disposed on the carrier to partly encapsulate the sensor device and partly encapsulate the protection element,
wherein the protection element includes the rod, and the free end of the rod protrudes from the encapsulation and extends in parallel to a planar surface of the carrier, and
wherein a portion of the protection element between the free end and the terminal end extends orthogonal to the planar surface of the carrier and represents a portion of the protection element that is encapsulated by the encapsulation.

11. The electronic component according to claim 10, wherein the protection element includes the rod, and the free end of the rod extends in parallel to a planar surface of the carrier, and a portion of the protection element between the free end and the terminal end extends orthogonal to the planar surface of the carrier and represents a portion of the protection element that is encapsulated by the encapsulation.

12. The electronic component according to claim 1, further comprising:
  a housing for protecting the sensor device,
  wherein the housing comprises one or more mounting elements, and the housing is mounted to the carrier via at least one of the one or more mounting elements.

13. An electronic component, comprising:
  a carrier;
  a sensor device mounted on the carrier, said sensor device comprising a sensor chip;
  an electrostatic discharge protection element mounted on the carrier, for protecting the sensor chip from an electrostatic discharge, the protection element comprising
    a bridging structure including at least two terminals resting on the carrier, wherein the protection element is arranged to bridge the sensor device, or
    a rod including a single terminal mounted on the carrier, wherein the rod includes a portion extending into a space above the sensor device; and
  a housing for the carrier,
  wherein the sensor device is not covered by the housing,
  wherein each of the at least two terminals comprises an extension arranged in a form fit with the housing.

14. The electronic component according to claim 13, wherein the carrier and the housing are held together by the protection element, and a horizontal portion of the protection element bridging the sensor device is arranged on a common level together with each of the extensions.

15. A method for manufacturing an electronic component, comprising:
  providing a sensor device including contact pads;
  providing an electrostatic discharge protection element including at least one terminal;
  arranging the sensor device on a carrier with the contact pads facing the carrier;
  arranging the protection element on the carrier with the at least one terminal facing the carrier, the protection element comprising
    a bridging structure including at least two terminals where the protection element is arranged to bridge the sensor device, and the at least two terminals rest on the carrier, or
    a rod including a free end and additionally including a terminal end forming a single terminal where a portion of the rod extends into a space above the sensor device and the single terminal is mounted on the carrier; and
  reflow soldering the contact pads and the at least one terminal in a common reflow soldering step.

16. The method according to claim 15, further comprising pressing or snapping or clipping the protection element in or to the carrier.

17. A method for manufacturing an electronic component, comprising:
  providing a sensor device including contact pads;
  providing an electrostatic discharge protection element including at least one terminal;
  arranging the sensor device on a carrier with the contact pads facing the carrier;
  arranging the protection element on the carrier with the at least one terminal facing the carrier, the protection element comprising
    a bridging structure including at least two terminals where the protection element is arranged to bridge the sensor device, and the at least two terminals rest on the carrier, or
    a rod including a free end and additionally including a terminal end forming a single terminal, a portion of the rod extends into a space above the sensor device and the single terminal is mounted on the carrier;
  prefabricating the sensor device by providing a sensor chip comprising a sensing element arranged on or integrated at a specific side of the sensor chip; and
  forming an encapsulation on the carrier to partly encapsulate the sensor device arranged on the carrier and partly encapsulate the protection element arranged on the carrier.

18. The method according to claim 17, further comprising:
  forming the encapsulation to comprise an ingress for providing access to the sensing element, wherein the encapsulation is formed on the carrier to make a portion of the protection element emerge from the encapsulation, the encapsulation being formed by arranging the carrier carrying the sensor device and the protection element into a mold comprising a plunger for pressing onto the protection element, and filling the mold by a mold compound resulting in the encapsulation including the ingress formed on the carrier by means of the plunger,
  wherein the mold is dimensioned with respect to the carrier carrying the sensor device and the protection element to deform the protection element by the plunger in response to closing the mold, and the protection element remains deformed after molding.

19. The method according to claim 18,
  wherein the protection element comprises the bridging structure including the at least two terminals resting on the carrier,
  wherein the encapsulation is formed to make the protection element at least partly bridge the ingress.

20. The method according to claim 17,
wherein the protection element comprises the rod and wherein
the free end of the rod protrudes from the encapsulation after molding and the free end having been bent after the encapsulation having been formed, resulting in an orientation in parallel to a planar surface of the carrier, and
a portion of the protection element between the free end and the terminal end extends orthogonal to the planar surface of the carrier and represents a portion of the protection element that is encapsulated.

21. The method according to claim 17, further comprising:
a step of partially encapsulating the sensor chip by a package comprising an access opening for providing access to the sensing element, wherein the sensor chip is arranged on a leadframe prior to the step of partially encapsulating, and wherein in the step of partially encapsulating, the leadframe is partly encapsulated by the package exposing portions of the leadframe representing the contact pads of the sensor device,
wherein the encapsulation partly encapsulating the sensor device and partly encapsulating the protection element arranged on the carrier partly covers the carrier, and is formed by one of:
injection molding;
low pressure injection molding;
hotmelt molding or potting;
transfer molding.

22. The method according to claim 15, further comprising:
automatically optically inspecting, by an automatic inspection device, solder connections, created in the reflow soldering step, between the contact pads and the carrier.

* * * * *